United States Patent [19]
Wawro et al.

[11] Patent Number: 6,130,520
[45] Date of Patent: Oct. 10, 2000

[54] DIAGNOSTIC INSTRUMENT SYSTEM

[75] Inventors: Marcia J. Wawro, Auburn; Ronald A. Hauptli, Warners; Michael Cariseo, East Syracuse, all of N.Y.

[73] Assignee: Welch Allyn, Inc., Skaneateles Falls, N.Y.

[21] Appl. No.: 09/265,170

[22] Filed: Mar. 9, 1999

Related U.S. Application Data

[60] Provisional application No. 60/078,005, Mar. 13, 1998.

[51] Int. Cl.$^7$ .................................. H02J 7/00; A61B 1/04
[52] U.S. Cl. .............................. 320/114; 600/110; 429/97
[58] Field of Search ................................... 320/107, 114; 429/97, 100; D13/107, 108

[56] References Cited

U.S. PATENT DOCUMENTS

| | | | |
|---|---|---|---|
| 3,005,090 | 10/1961 | Moore ....................................... | 320/113 |
| 3,698,387 | 10/1972 | Moore et al. ............................ | 600/200 |
| 3,829,676 | 8/1974 | Nelson et al. ............................ | 320/115 |
| 4,006,738 | 2/1977 | Moore et al. ............................ | 600/200 |
| 4,115,842 | 9/1978 | Keller ....................................... | 362/183 |
| 4,147,163 | 4/1979 | Newman et al. ......................... | 320/114 |
| 4,991,069 | 2/1991 | Tyler ......................................... | 362/183 |
| 5,177,424 | 1/1993 | Connors ................................... | 320/114 |
| 5,221,457 | 6/1993 | North et al. .............................. | 204/416 |
| 5,410,237 | 4/1995 | Sharrah et al. .......................... | 320/115 |
| 5,429,119 | 7/1995 | Griffin et al. ............................ | 600/200 |
| 5,527,261 | 6/1996 | Monroe et al. .......................... | 600/109 |
| 5,542,904 | 8/1996 | Heine et al. .............................. | 600/197 |
| 5,918,187 | 6/1999 | Weng ........................................ | 320/114 |
| 5,973,476 | 10/1999 | Irvin ......................................... | 320/114 |
| 6,002,236 | 12/1999 | Trant et al. ............................... | 320/114 |

Primary Examiner—Peter S. Wong
Assistant Examiner—Pia Tibbits
Attorney, Agent, or Firm—Wall Marjama & Bilinski

[57] ABSTRACT

A handle for a diagnostic instrument includes a battery housing for retaining at least one rechargeable battery and a set of interchangeable adapters which can be selectively and releasably engaged with the housing to allow recharging of the battery through interconnection with an external power source, such as a wall outlet. The adapters are directly attached and detached to one end of the battery housing without requiring any disassembly or modification of the battery housing, allowing the instrument to be used either with or without an attached adapter.

31 Claims, 8 Drawing Sheets

DIAGNOSTIC INSTRUMENT SYSTEM

CROSS REFERENCE TO RELATED APPLICATIONS

This is a non-provisional application based upon U.S. Ser. No. 60/078,005, filed Mar. 13, 1998.

FIELD OF THE INVENTION

The invention relates to the field of diagnostic instruments, and more particularly to a hand-held diagnostic instrument system which includes a set of interchangeable adapters. Each adapter is releasably attachable to the handle of the instrument to allow recharging of a contained battery without requiring disassembly of the handle. In addition, the instrument can selectively incorporate the adapter as part of the handle after attachment.

BACKGROUND OF THE INVENTION

Health professionals use a variety of small hand-held diagnostic instruments such as otoscopes, ophthalmoscopes and retinoscopes, among others, for performing specific examinations. Battery operated versions of such instruments are known, such as those described in U.S. Pat. Nos. 3,698,387 and 4,006,738 issued to Moore et al, U.S. Pat. No. 4,147,163 issued to Newman et al, and U.S. Pat. No. 5,117,424, issued to Connors. Each of the instruments described in these patents includes a grippable handle containing rechargeable batteries and a suitable instrument head that is removably attached to the top end of the handle.

As described in the latter '424 patent, interchangeable adapters can be attached to the handle to allow the contained batteries to be recharged without requiring the batteries to be removed from the instrument. The adapters include a transformer suitable for allowing the batteries contained within the handle to be recharged using either a domestic 120 volt using one of the adapters or a foreign 220 volt outlet when using another adapter. Another exemplary diagnostic instrument utilizing interchangeable adapters is described in U.S. Pat. No. 5,542,904, issued to Heine et al. In each reference, however, at least partial disassembly of the gripping handle is required in order to install the adapter of choice, this disassembly is rather cumbersome, time-consuming, and awkward.

There is an identified need to provide a battery powered diagnostic instrument which allows the contained batteries to be recharged from a variety of different power sources but without requiring removal of the batteries or disassembly or teardown of the instrument handle.

SUMMARY OF THE INVENTION

A primary object of the present invention is to improve the state of the art of diagnostic instruments.

A further primary object of the invention is to provide a handle for a hand-held battery-powered diagnostic instrument which can be easily recharged without requiring removal of the battery from the handle or teardown of the instrument.

It is another primary object of the present invention to provide a battery-powered diagnostic instrument in which the batteries can selectively be recharged from a variety of different power sources.

Therefore, and according to a preferred aspect of the present invention, there is provided a handle for a hand-held battery-powered diagnostic instrument, said handle including a casing sized for containing at least one rechargeable battery; and at least one battery-charging adapter individually and releasably attachable to said handle, said at least one adapter being engageable with said handle to allow recharging of said at least one battery without requiring disassembly of the casing.

Preferably, a set of interchangeable adapters used in connection with the above handle are provided, each of the adapters allowing the stored battery to be charged using different power sources, lending flexibility in the continued use of the diagnostic instrument.

A feature of the invention is that at least one of the interchangeable adapters includes a transformer having a set of prongs which are engageable with a wall outlet or other exterior power supply, wherein the prongs can be selectively deployed and stored within the interior of the adapter when not needed.

According to another preferred aspect of the present invention, there is provided a diagnostic instrument comprising:

a handle including a battery housing having a hollow interior sized for retaining at least one rechargeable battery; and at least one adapter releasably engageable with said battery housing, said at least one adapter containing means for recharging said battery in connection with an exterior power source, wherein said at least one adapter is attached to and released from said housing without requiring any disassembly of the instrument.

Preferably, several interchangeable adapters are provided, each adapter allowing the retained batteries to be selectively recharged from one of several different exterior power sources, such as a 110 or 220 volt outlet, wall transformer, charging stand, or the like.

According to a preferred embodiment, the adapters commonly engage a bottom end of the battery housing to provide electrical contact between the exterior power supply and the contained battery. In the case of using a 110 or 220 volt wall outlet, a transformer is included in the adapter body which includes a set of electrical prongs for engaging the wall outlet.

A feature of the present invention is that the handle can incorporate an adapter as a part of the handle, wherein the battery housing is not opened during assembly and teardown of the adapters.

An advantage of the present invention is that each of the adapters of the described system can be releasably attached to the handle without requiring disassembly; that is, opening of the battery handle. The adapters can remain with the instrument to be part of the handle, or the instrument can operate without requiring any of the adapters to be attached thereto.

A further advantage of the present invention is that the battery housing is designed as a uniquely separate unit, which can be discarded after a predetermined number of uses.

These and other objects, features and advantages will become apparent from the following Detailed Description of the Invention, which should be read in conjunction with the accompanying drawings.

DETAILED DESCRIPTION

The following description relates to certain preferred diagnostic instrument systems in accordance with the present invention. Throughout the course of the discussion which follows, certain terms such as "top", "bottom", "upper", "lower", and the like are used to provide a frame of reference with regard to the accompanying drawings. These terms are not intended to be limiting of the concepts of the inventive concepts described herein.

Figure 1:
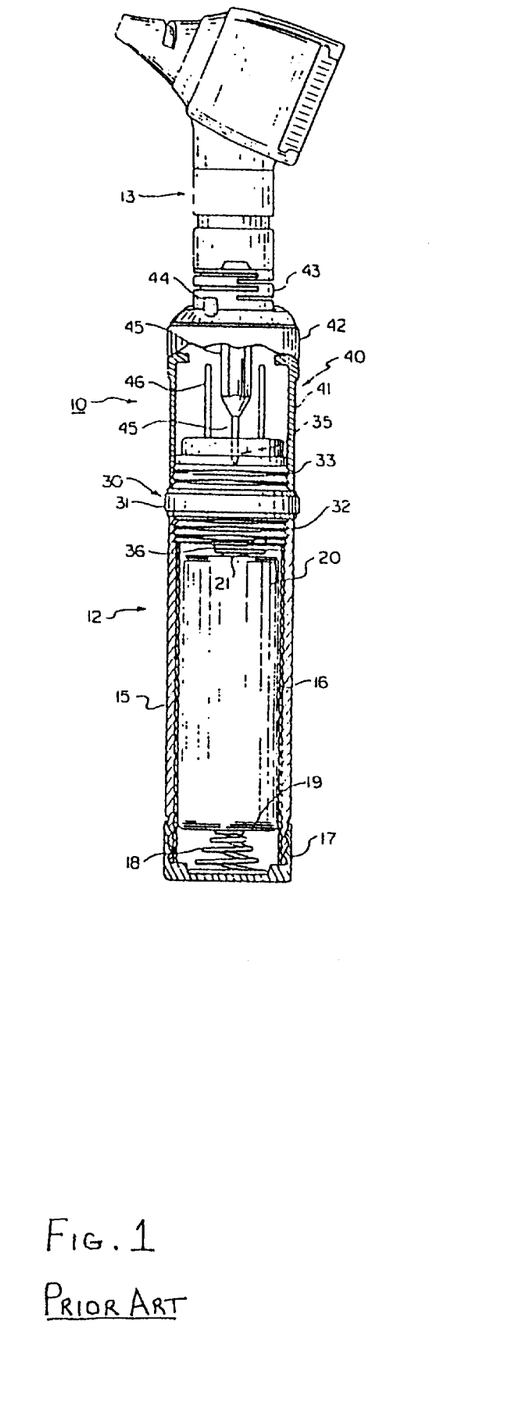
FIG. 1 is a side elevational view, in partial section, of a diagnostic instrument having a battery handle and an interchangeable adapter for use with a rechargeable battery contained within the instrument according to the prior art.

To provide a better background and to more fully detail the novel contributions of the present invention, reference is herein made to FIG. 1, which illustrates a battery-powered diagnostic instrument according to the prior art, which is generally referenced herein as 10.

The diagnostic instrument 10 contains two main sections; namely, a battery handle 12 and an instrument head 13 that is removably attached to the battery handle. The instrument head illustrated is that of an otoscope, however, the handle can be used interchangeably with any number of instrument heads, such as those presently manufactured by Welch Allyn, Inc of Skaneateles Falls, N.Y. Typically, the instrument head 13 will minimally contain a light source such as a halogen or other incandescent lamp (not shown) for illuminating a target of interest.

The battery handle 12 includes a tubular battery casing 15 made of a conductive metal that serves as an electrical ground in the battery powered circuit. The lower or proximal end of the battery casing 15 is closed by an end cap 17 that is removably threaded onto the casing. The end cap 17 contains a helically-wound spring 18 that is adapted to contact the bottom surface or negative terminal 19 of a rechargeable battery 20 housed within the casing 15 and thus connect the negative terminal to ground. According to this embodiment, a non-conductive sleeve 16 is contained within the casing 15 to prevent a rechargeable battery having a side protruding terminal from electrically contacting the casing and therefore shorting out the battery.

An adapter 30 is threaded onto the top of the battery casing 15 and includes a centrally located flange 31, a lower or proximal threaded section 32 which is threaded onto the casing and an upper or distal threaded section 33 which is threaded into a connector housing 40. The connector housing 40 has a tubular body 41 which is adapted to mate with the upper threaded portion 33 of the adapter 30 and further includes an end closure 42 upon which an axially extended bearing is supported. The instrument head 13 includes a bayonet portion 43 for attaching to the top end of the connector housing 40. An ON/OFF switch 44 located on the end closure 42 of the connector housing 40 functions to open and close the electrical path between the instrument head and a pin connector probe 45. The pin connector probe 45, according to this device, extends downwardly, ie., proximally from the end closure 42 into the housing where it is received within a socket 35 located in the top wall of the adapter 30. Although not shown, the socket 35 is electrically connected to an electrical pad 36 mounted on the bottom wall of the adapter 30. The pad 36 is arranged to make contact with the distal terminal 21 (positive) of the battery 20, and thus complete the circuit to provide electrical power to the instrument head.

The adapter 30 has a pair of prongs 46—46 extending distally from the upper surface thereof. The prongs, in assembly, pass upwardly and are situated on either side of the pin connector probe 45. A transformer (not shown) is arranged within the adapter 30 to step down a 120 or 220 volt input to a desired battery voltage. Details relating to the above are provided in U.S. Pat. No. 5,177,424, the entire contents of which are herein incorporated by reference.

In use, and to recharge the battery 20, the adapter connector housing 40 is unscrewed from the adapter 30 to expose the electrical prongs 46—46. The prongs 46—46 can then be connected into any conventional wall outlet (not shown) for a sufficient period of time in order to bring the battery 20 up to its operating level.

Therefore, and in order to recharge the battery 20, the handle must be partially disassembled from the instrument 10 in order to expose the prongs 46—46. Likewise, and as described in U.S. Pat. No. 5,542,904, the end cap at the bottom of the handle is removed in order to place any of the interchangeable adapters in place. Each adapter according to this reference replaces the end cap of the handle when the instrument is being recharged.

Figure 2:
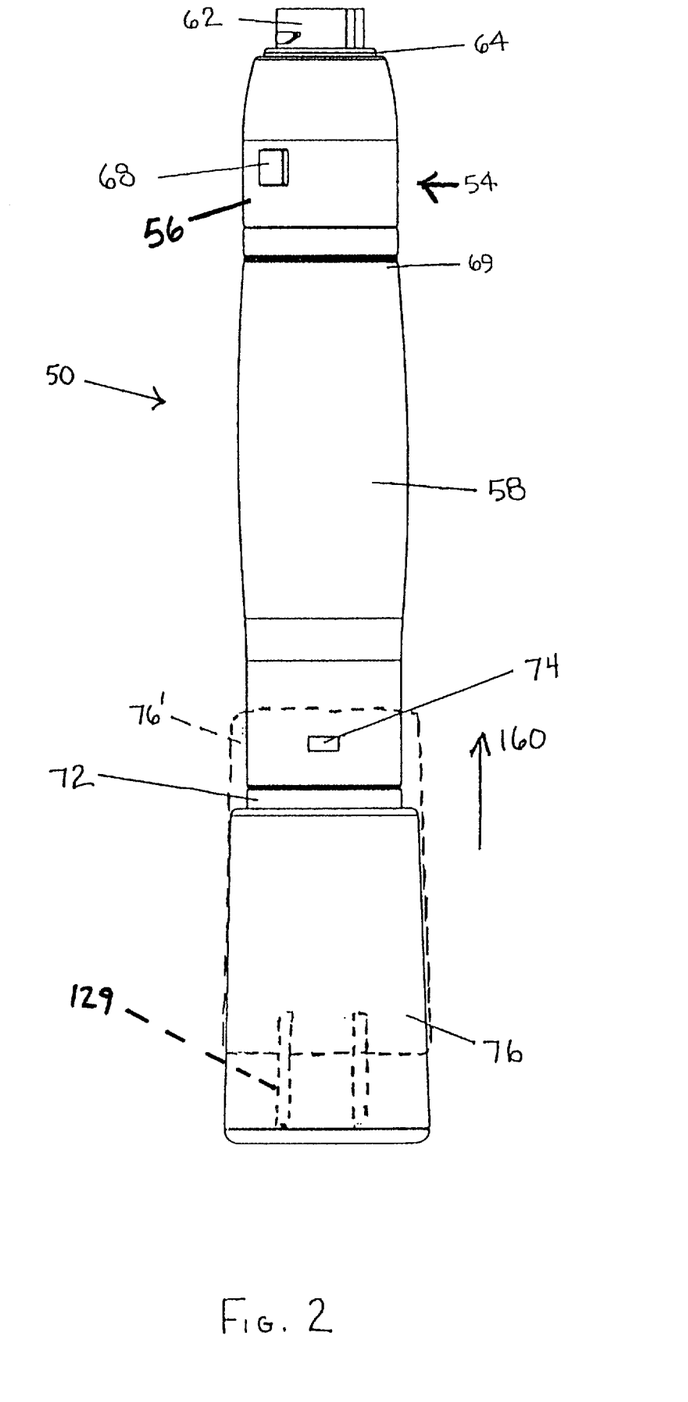
FIG. 2 is a side elevational view of a diagnostic instrument and attached adapter made in accordance with a preferred embodiment of the present invention.

With this background, reference is now made to FIG. 2, which illustrates a diagnostic instrument handle 50 in accordance with a preferred embodiment of the present invention. The handle 50 includes a two-part assembly comprising an upper rheostat section 54 and a lower battery housing section 58. An instrument head (not shown) is releasably attached to a connector 62 disposed at the upper end 64 of the rheostat section 54. The instrument head for purposes of this discussion is similar to that described in the previously incorporated U.S. Pat. No. 5,117,424, and does not form an essential part of this invention.

In brief, the rheostat portion 54 is releasably attached at the upper end 69 of the battery housing 58 and includes circuitry for powering a lamp (not shown) provided in the instrument head (not shown). A button 68 disposed on the exterior of the rheostat portion cooperates with a rotatable section 56 for controlling the amount of illumination from the lamp assembly (not shown) of the instrument head. As previously noted, each of the above features are found in hand-held diagnostic instruments, such as those cross referenced above, and are commonly known. Therefore, no further discussion of these features is required, as they do not form an essential part of the present invention.

A light emitting diode (LED) (not shown) disposed within a cavity or compartment of the battery housing section 58 adjacent the lower end 72 utilizes a light pipe 74 to act as a low battery indicator, as is described in greater detail below. A set of interchangeable adapters (only a single adapter 76 is shown and described herein) are selectively engageable with the lower end 72 of the battery housing section 58. Each of the above will be described in greater detail below, but at this point of the discussion, the battery housing section 58 will first be described in greater detail with particular reference to FIGS. 2–4.

Figure 3:
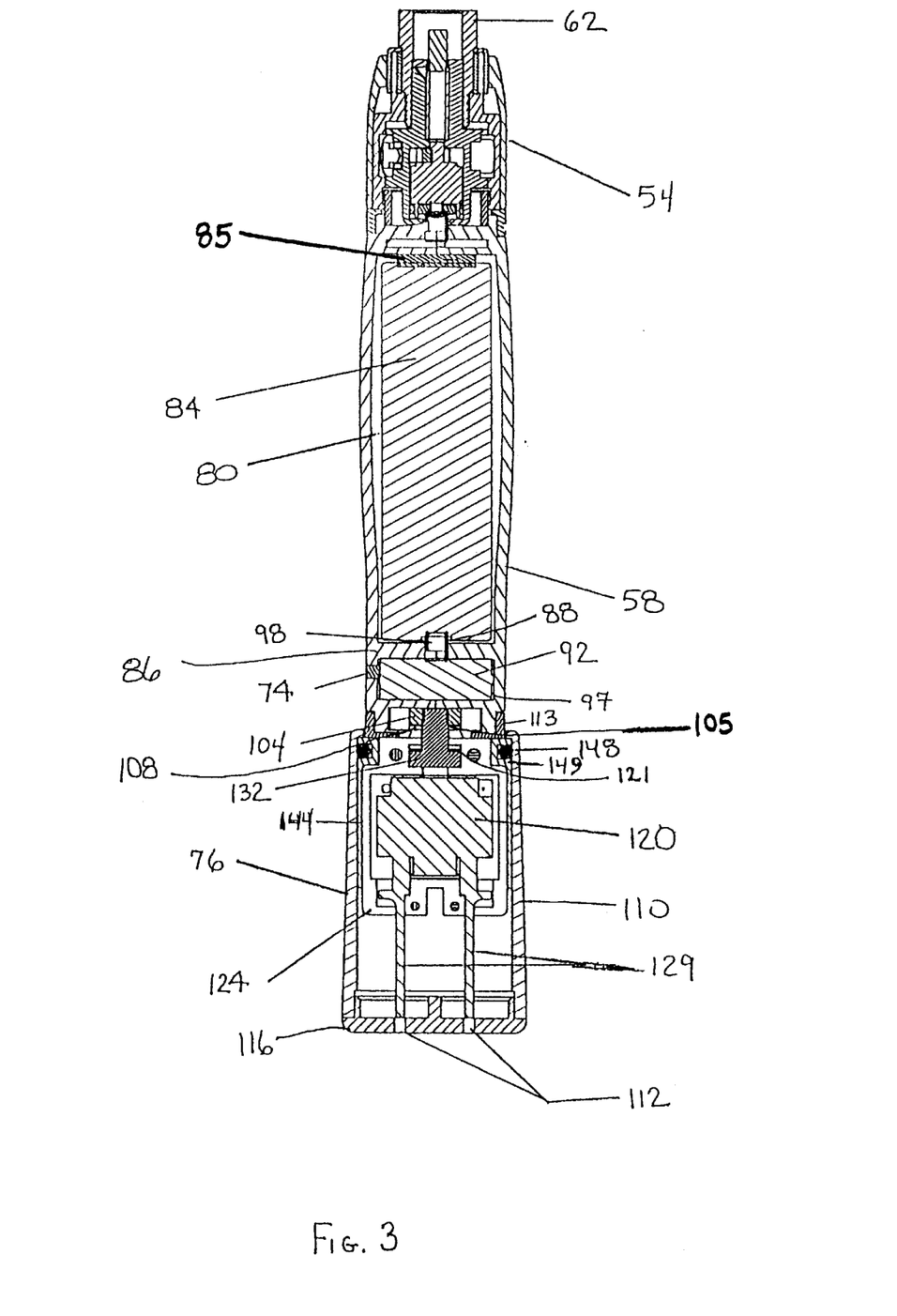
FIG. 3 is the side elevational view of FIG. 2, in section showing the connection of the adapter and the battery housing of the handle.
Figure 4:
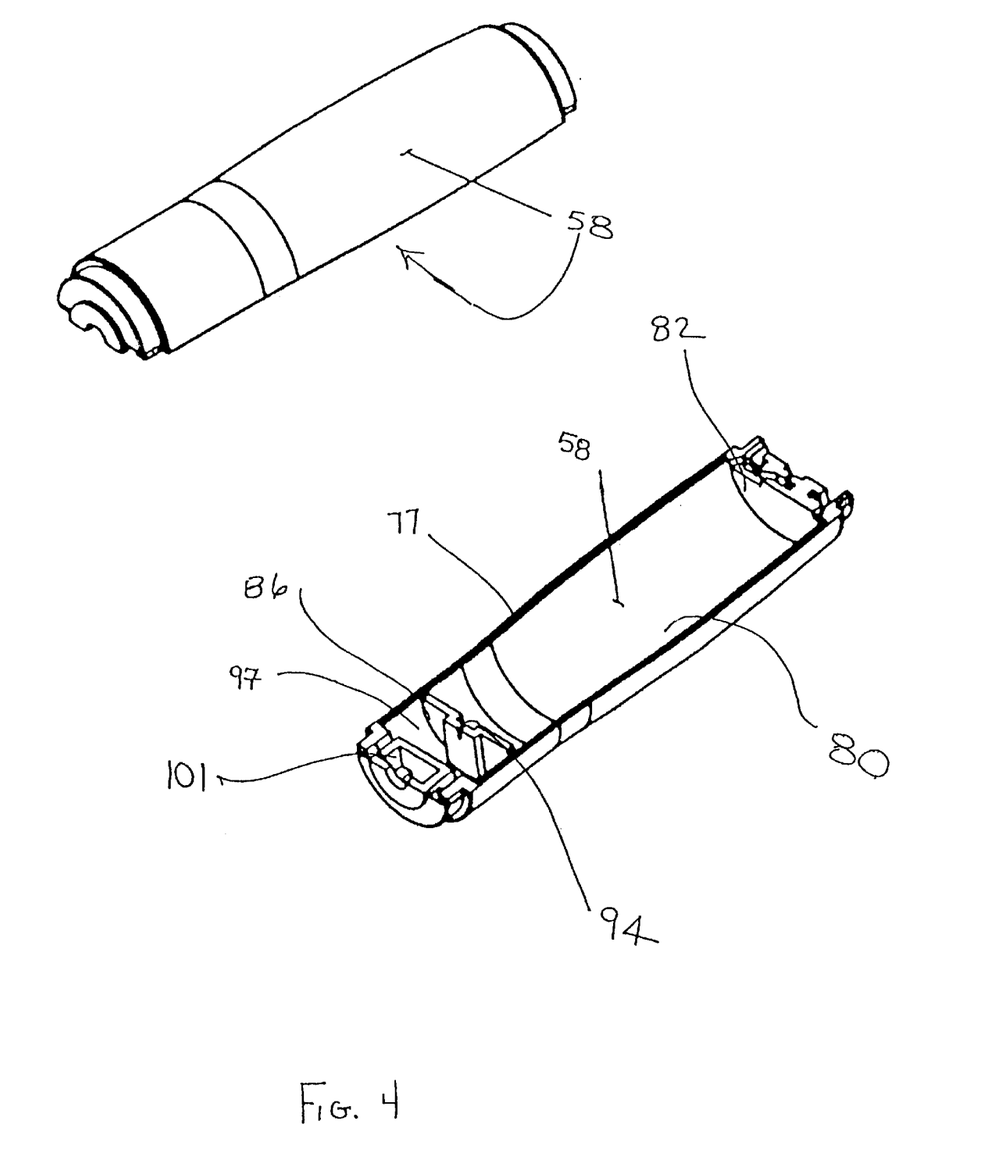
FIG. 4 is an exploded view of the exterior of the battery housing of the handle of a diagnostic instrument and attached adapter made in accordance with a preferred embodiment of the present invention.

The battery housing section 58 is a hollow cylindrical two-part molded plastic member having a hollow interior battery compartment 80 defined by the cylindrical wall 77 of the two piece housing and a pair of spaced partitions 82, 86. The compartment 80 is appropriately sized for retaining a battery 84 in a vertical configuration. According to the present invention, a 3.6 Volt lithium-ion battery having protection circuitry, such as those manufactured by Sanyo Corp, is used which is relatively compact, the battery having a length of less than 3 inches. The positive terminal 88 of the battery 84 is positioned in the lower or proximal end of the compartment 80 and is biased by a contact spring 98 disposed in a center recess 94 on the distal or upper side of the lower spaced partition 86. The upper terminal of the battery 84 is biased into contact with a separate contact spring and a foam pad 85 as is commonly known.

The battery housing portion 58 includes a separate molded cavity 97 in the lower end 72 thereof immediately beneath the battery compartment 80 for retaining a printed circuit board 92 to which the above mentioned light emitting diode (not shown) is soldered or other attached, the light pipe 74 being adjacent to the LED and extending into a small through opening provided in the wall of the battery housing section 58. The contact spring 98 is also attached by known means to the PC board 92.

A steel nut 104 is disposed within another molded cavity 101 adjacent the lower end of the housing section 58 and beneath the PC board 92. The nut 104 includes a threaded opening 105 sized for engagement by a connected adapter 76, the description of which follows below. A thin metal contact plate 108, made preferably from a spring material which is electrically conductive is attached to the nut 104, in which according to this embodiment a contact portion covers the lower or proximal face of the nut and includes a center through opening (not shown) aligned with the threaded opening 105 of the nut and having an extending portion (not shown) which engages the PC board 92. Finally, a circular metal retaining plate 113 is attached, snap-fitted according to the present embodiment, to the lower end of the battery housing section 58. When assembled, the nut 104 is accessible through a center opening 115 in the bottom face of the battery housing section 58.

Figure 5:
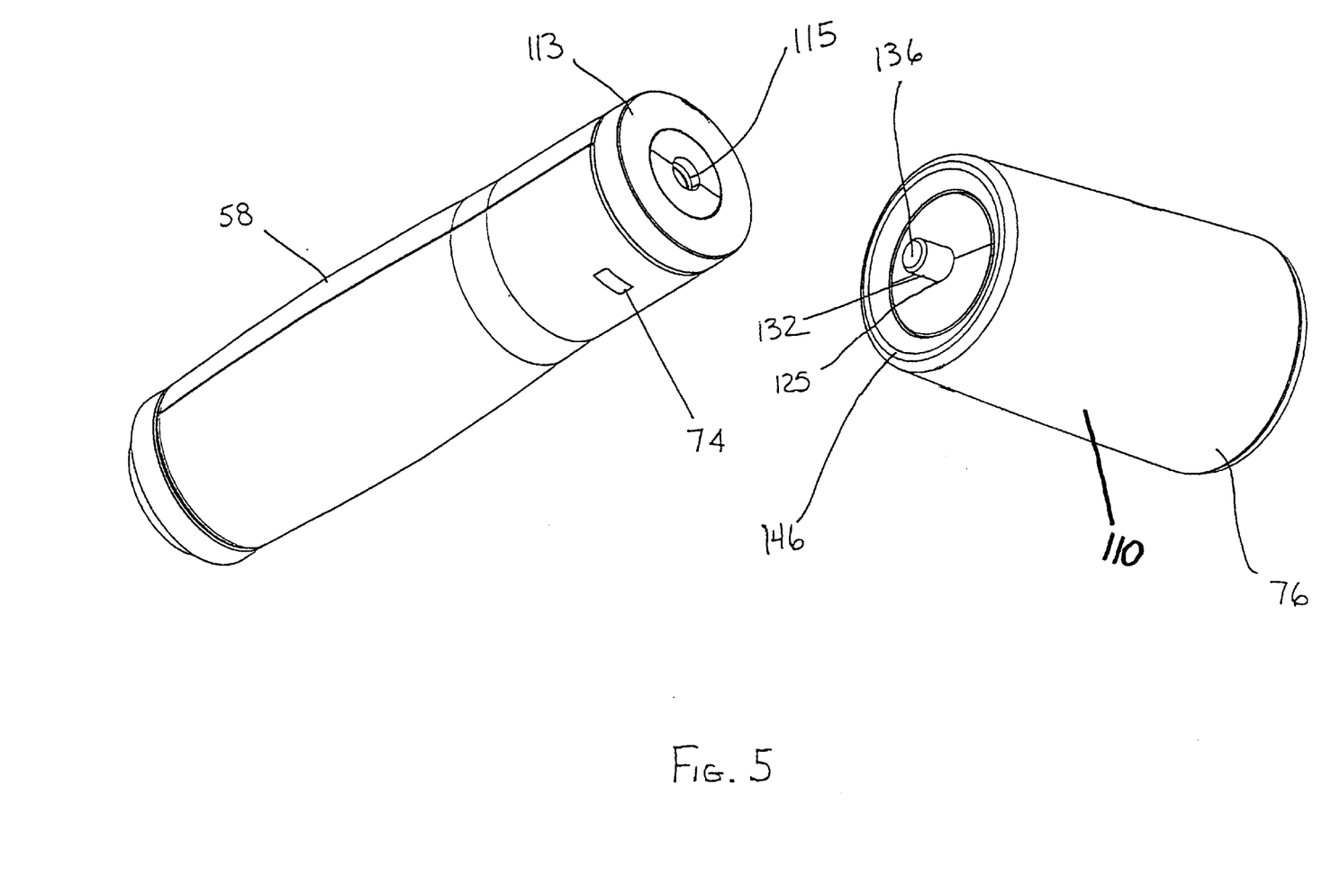
FIG. 5 is a partial isometric view of the instrument handle of FIGS. 2–4 with an adjacent adapter.

Referring to FIGS. 2, 3, and 5, the adapter 76 is defined by an exterior plastic sleeve 10 having a slightly tapering cylindrical cross section including a pair of spaced slotted openings 112 in a bottom surface 116 thereof. A transformer 120, similar in function to that described in previously incorporated U.S. Pat. No. 5,177,424, or equivalent is disposed within the adapter body 76 and is fitted therein by conventional means. The transformer 120 includes a pair of prongs 129 extending downwardly therefrom through openings provided in a plastic molded insulator 124 which essentially covers and retains the transformer 120. The insulator 124 includes a cavity 121 adjacent the distal or upper end of the adapter 76 for retaining a bolt member 132, the bolt member having an extending threaded end 136 which passes through a distal opening 125 of the adapter 76 as most clearly seen in FIG. 5. Finally, a conductive shell 144 is provided between the inner wall of the sleeve 110 and the plastic insulator 124, the shell according to this embodiment being made of brass, and including an annular portion 146 provided on the distal face of the adapter 76. An O-ring 148 is provided in an inwardly extending annular slot 149 provided on the shell 144.

The adapter 76 is attached by aligning and engaging the extending end 136 of the bolt member 132 with the opening 115 in the lower end 72 of the housing section 58. The engagement of the bolt member 132 with the internal threads of the nut 104 provides positive mechanical engagement, as well as electrical contact due to the contact plate 108, the circuit being completed when the adapter 76 has been fully engaged with the nut 104 via clockwise rotation relative to the handle until the metal retaining plate 113 is placed in contact with the annular portion 146 on the distal face of the adapter 76.

Rotation of the adapter 76 moves the holes 112 on the bottom face 116 into alignment with the prongs 129 of the transformer 120, allowing the adapter, shown as 76', to be moved vertically in the direction 160 shown in FIG. 2, thereby exposing the prongs. The battery 84 can then be charged by engagement of the prongs 129 with a wall outlet or other suitable power supply (not shown) for a predetermined period of time.

The adapter 76 can be removed by reversing the procedure. That is, the prongs 129 can be retracted by sliding the adapter sleeve 110 downwardly relative to the instrument handle and rotating the sleeve until the holes 112 are out of alignment therewith. The adapter 76 can then be removed by simply grasping and rotating the adapter in a counterclockwise direction against a fixed handle.

Though not shown, other adapters can be provided for use with the above battery housing section 58. For example, adapters utilizing similar circuitry and employing the same attachment mechanism can be developed to charge the battery relative to a 220 volt outlet, the adapter being configured to interface with a wall or table-top charging unit, such as those manufactured and sold by Welch Allyn, Inc., including those described in U.S. Pat. No. 3,005,090, or to charge the battery relative to a wall transformer. In another preferred embodiment, the handle 50 can be modified so as to directly interface with the mounting pins (not shown) of a desk-top charging unit without requiring the use of an adapter.

When used in the above manner, the adapter(s) can remain attached to serve as an extension of the instrument handle or which can be removed therefrom, without interfering with the overall operation of the instrument.

Figure 6:
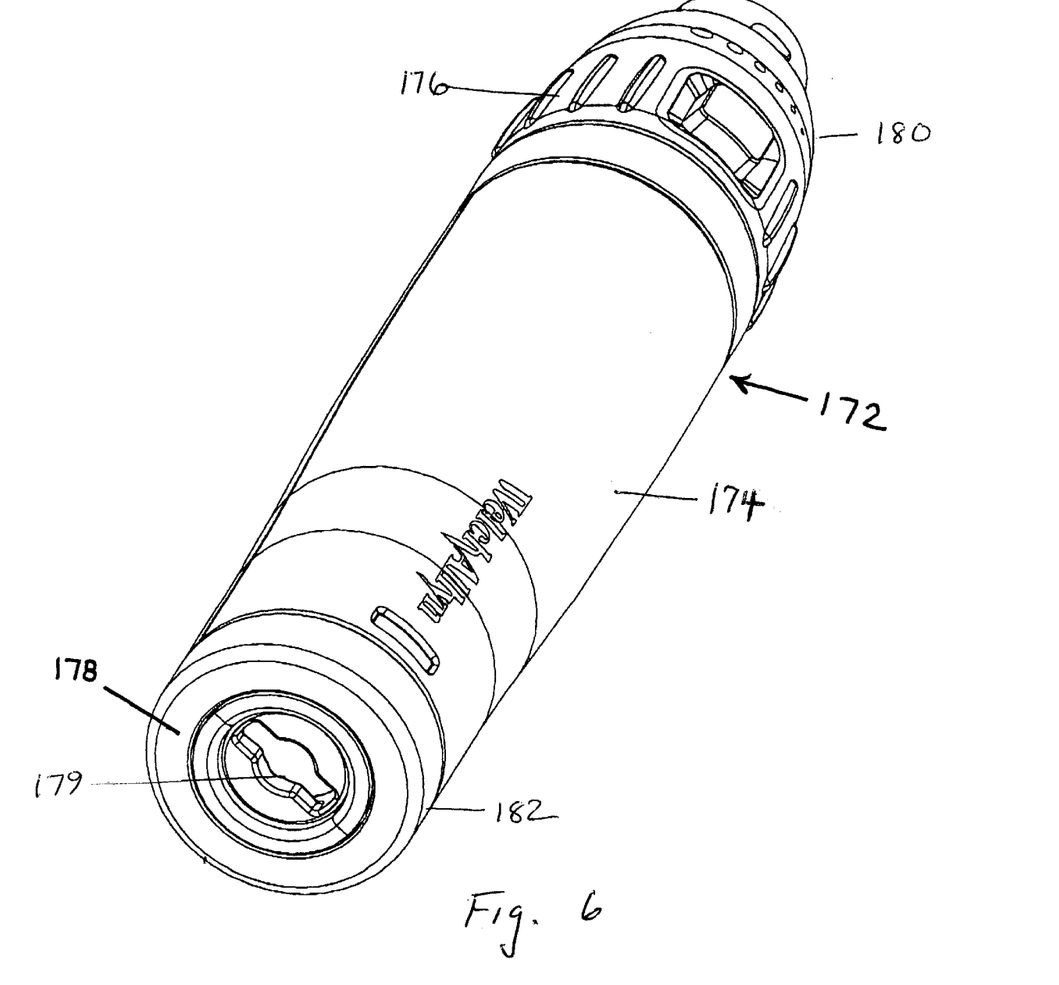
FIG. 6 is a bottom perspective view of a diagnostic instrument handle according to a second preferred embodiment of the invention.
Figure 7:
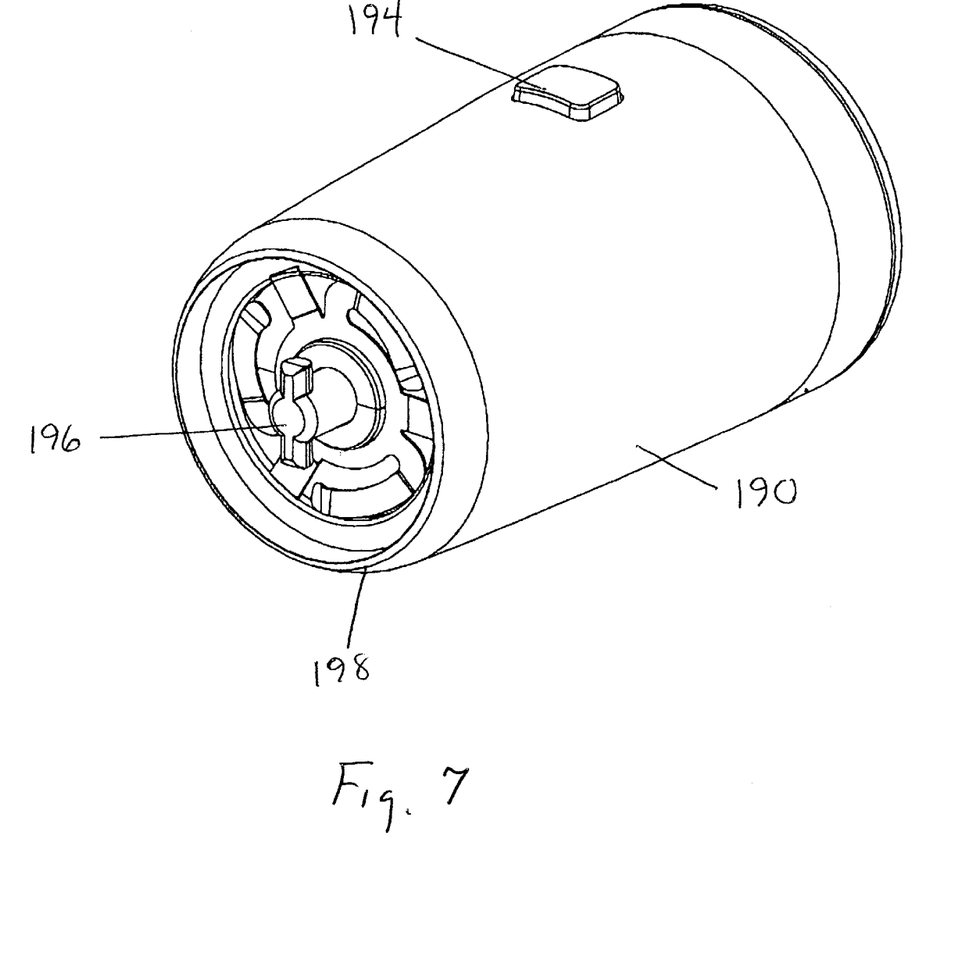
FIG. 7 is a top perspective view of an adapter made in accordance with the second embodiment.
Figure 8:
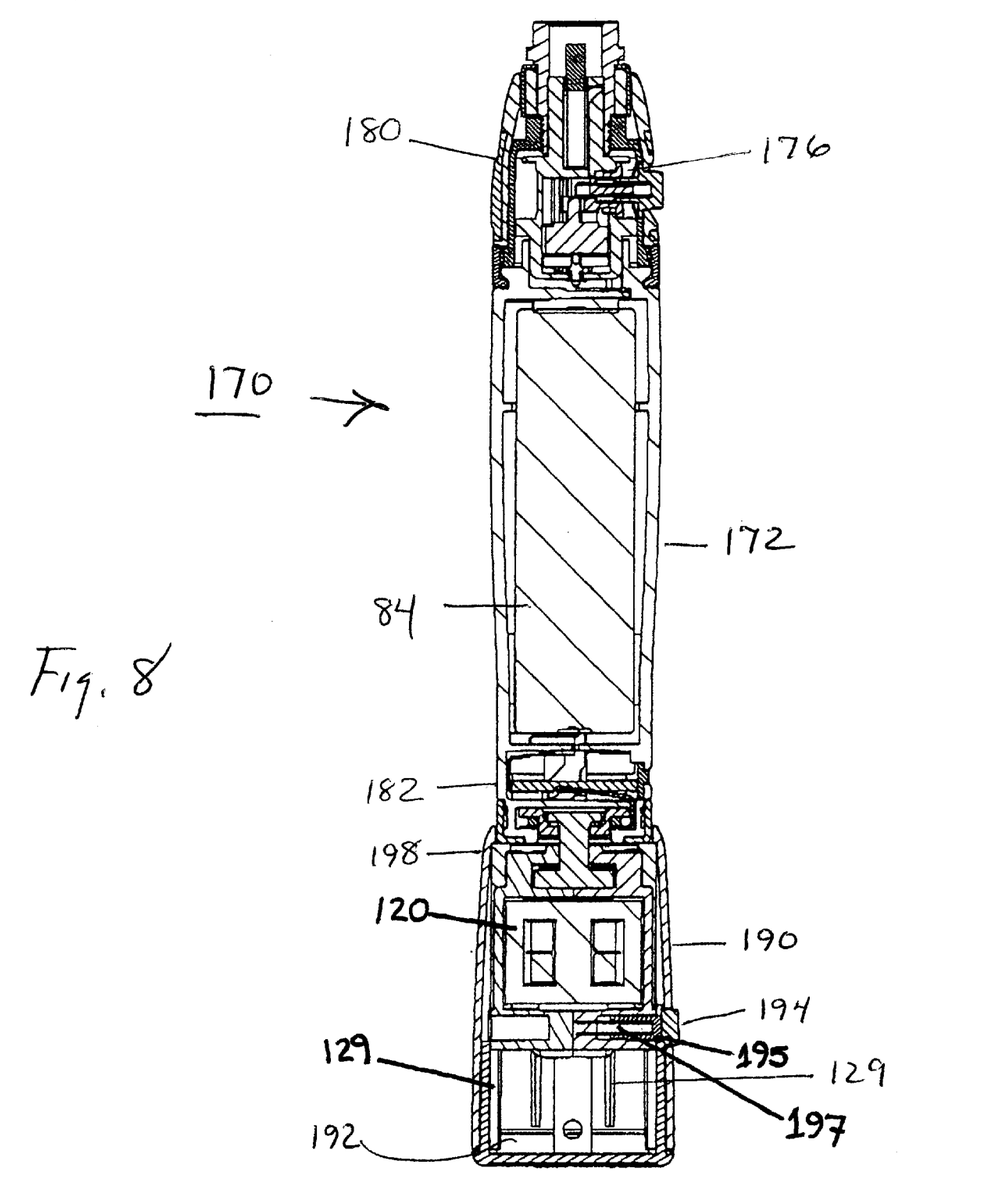
FIG. 8 is a sectional view of the diagnostic handle of FIG. 6 having the attached adapter of FIG. 7.

Referring to FIGS. 6–8, a diagnostic instrument handle assembly 170 in accordance with a second preferred embodiment is herein described.

Referring to FIGS. 6 and 8, the handle portion 172 includes a battery casing 174 having a rheostat portion 176 at one upper end 180 and an engagement portion 178 at an opposing lower end 182. As in the preceding, a battery 84 is housed within the casing 174.

Referring to FIGS. 7 and 8, an adapter 190 is releasably attachable to the engagement portion 178 of the handle portion 172. The adapter 190 is similar to that described in the first embodiment having an interior 192 which is tapered to conform to the handle portion 172 and which includes a transformer 120 and a set of prongs 129, each having essentially each of the features previously described. In this embodiment, an exterior button 194 provided on the exterior of the adapter 190 is used as a safety interlock to selectively expose or deploy the prongs 129 contained therein, as described below.

A T-shaped engagement member 196 extends from the distal end 198 of the adapter 190 which is sized for engaging a keyway 179 provided on the engagement portion 178 of the handle portion 172. Engagement of the T-shaped engagement member 196 with the keyway 179 provides an electrical contact with the contained battery 84 such that the battery can be recharged when the prongs 129 are deployed and engaged, for example, with a wall outlet (not shown).

In operation, the adapter 190 is attached by engaging the T-shaped engagement member 196 of the adapter into the keyway 179 of the handle portion 172 and twisting to lock the adapter in place. Depression of the exterior button 194 overcomes a biasing force supplied by a spring 195 and releases the prongs by sliding a pin 197 or other support member which retains the set of prongs 129 within the adapter interior 192. The prongs 129 are preferably aligned with a set of openings (not shown) provided in the bottom of the adapter 190. Simultaneously depressing the button 194 and pushing the body of the adapter toward the instrument head (not shown) will cause the outer shell of the adapter to act as a sleeve which slides over the bottom end of the handle portion 172, thereby exposing the prongs 129 in a deployed position. A suitable electrical connection with the retained battery 84 is created when the adapter has been attached to the handle, allowing recharging thereof when the prongs 129 are engaged with a power supply (not shown).

The adapter 190 is removed by reversing the above procedure by sliding the adapter sleeve downwardly away from the instrument head (not shown) after the battery 84 has been recharged and the assembly has been disconnected from the power supply (not shown). This movement thereafter causes the prongs 129 to be directed into the adapter interior 192 and causes the pin 197 to reengage and lock the prongs therein, with the button 194 being reset. The adapter 190 can then either be removed or retained relative to the handle portion 172 at the user's option.

PARTS LIST FOR FIGS. 1–8

10 battery-powered diagnostic medical instrument
12 battery handle
13 instrument head
15 tubular battery casing
16 non-conductive sleeve
17 end cap
18 compression spring
19 negative battery terminal
20 battery
21 positive battery terminal
30 adapter
31 centrally located flange
32 lower (proximal) threaded section
33 upper (distal) threaded section
36 electrical pad
40 connector housing
41 tubular body
42 end closure
43 axially-extended coupling
45 pin connector
46 prongs
50 diagnostic instrument handle
54 rheostat portion
56 rotatable portion
58 battery housing
62 connector
64 upper end—rheostat portion
68 button
69 upper end—battery housing
72 lower end—battery housing
74 light pipe
76 adapter
76' adapter
77 cylindrical wall
80 interior battery compartment
82 plate
84 battery
85 foam pad
86 plate
88 positive terminal
92 PC board
94 center recess
97 cavity
98 contact spring
101 cavity
104 nut
105 threaded opening
108 contact plate
110 plastic sleeve
112 slotted openings
113 retaining plate
115 center opening
116 bottom face
120 transformer
121 cavity
124 plastic insulator
125 distal opening
129 prongs
132 bolt member
144 conductive shell
146 annular portion
148 O-ring
149 annular slot
160 direction
170 handle assembly
172 handle portion
174 battery casing
176 rheostat portion
178 engagement portion
179 keyway
180 upperend
182 lower end
190 adapter
192 interior
194 exterior button
195 spring
196 T-shaped engagement member
197 pin
198 distal end While this invention has been explained with reference to the structure disclosed herein, it is not confined to the details set forth and this application is intended to cover any modifications and changes as may come within the scope of the following claims.

What is claimed is:

1. A handle for a hand-held diagnostic instrument, said diagnostic instrument including an instrument head attachable to a top end of said handle for examining a medical target, said handle comprising:

a battery housing having an interior sized for retaining at least one rechargeable battery for powering said instrument head; and at least one battery-recharging adapter including releasable attachment means for releasably attaching said at least one adapter to said battery housing and electrical interconnecting means contained within an adapter housing for electrically interconnecting with said at least one retained battery when said at least one adapter is attached to said housing, wherein attachment of a said adapter and recharging of said at least one retained battery does not require any disassembly of said battery housing and permits the diagnostic instrument to be used to examine a medical target while said at least one adapter is attached to said battery housing.

2. A handle as recited in claim 1, wherein said at least one adapter is a detachable part of the handle and in which said diagnostic instrument can be used to examine a medical target whether or not said at least one adapter is attached to said battery housing.

3. A handle as recited in claim 1, wherein said at least one adapter includes recharging means for recharging said at least one rechargeable battery, said recharging means including a transformer and a set of prongs extending from said transformer for connecting to a power supply, said at least one adapter including an adapter housing and prong deployment means for selectively exposing said prongs relative to said adapter housing to allow engagement with said power supply.

4. A handle as recited in claim 3, wherein said adapter housing includes a hollow interior into which said recharging means are disposed, said adapter housing having an axial dimension which is longer than a corresponding axial dimension of said recharging means, said prong deployment means permitting said recharging means to be slidingly movable relative to the hollow interior of said adapter housing.

5. A handle as recited in claim 4, wherein said releasable attachment means are interconnected to said recharging means such that said transformer and said set of prongs are fixed when said at least one adapter is attached to said battery housing wherein the adapter housing is slidingly movable relative to said battery housing and said recharging means to deploy said prongs for interconnection with said power supply.

6. A handle as recited in claim 5, wherein said prong deployment means includes interlock means for preventing said prongs from deployment from the hollow interior of said adapter housing.

7. A handle as recited in claim 6, wherein said adapter housing includes a bottom surface, said interlock means including a pair of spaced openings in said bottom surface which are initially misaligned with said prongs when said adapter is in a first attachment position, said adapter being rotatable to allow said prongs to be aligned with said openings when said adapter has been rotated to a second attachment position.

8. A handle as recited in claim 6, wherein said interlock means includes at least one pin member interconnecting said adapter housing and said recharging means and preventing relative movement therebetween and actuable switch means disposed on the exterior of said adapter housing connected to said pin member for selectively disconnecting said adapter housing from said recharging means and allowing said prongs to be exposed.

9. A handle as recited in claim 1, wherein said adapter attachment means includes a T-shaped engagement member provided on said one end of at least one battery-charging adapter for releasably engaging a keyway provided on the second end of said battery housing.

10. A handle as recited in claim 1, wherein said releasable attachment means includes at least one attachment member provided on one of said battery housing and said adapter for engaging an opening provided on the other of said battery housing and said adapter.

11. A diagnostic medical examination instrument system comprising:

a diagnostic medical examination instrument including a hand-grippable handle including a battery housing having a hollow interior sized for retaining at least one rechargeable battery;

an instrument head attachable to one end of said handle for examining a medical target of interest, said instrument head being powered by said at least one rechargeable battery; and at least one battery-charging adapter releasably engageable with said handle, said at least one battery-charging adapter containing an adapter housing, recharging means for recharging at least one battery retained in said handle and releasable engagement means for allowing said adapter housing to be attached to one end of said battery housing and form part of said handle when attached thereto, wherein said recharging means includes a transformer and a set of prongs extending from said transformer, said prongs being selectively deployable from said at least one adapter housing for engagement with a power supply and in which said at least one adapter permits recharging of said at least one rechargeable battery without disassembly of said battery housing.

12. An instrument system as recited in claim 11, wherein said adapter housing includes a hollow interior into which said recharging means are disposed, said adapter housing being slidingly movable relative to said recharging means to deploy said prongs from said adapter housing.

13. An instrument system as recited in claim 12, wherein said releasable engagement means are interconnected to said recharging means such that said transformer and said set of extending prongs are fixed axially when said at least one adapter is attached to said battery housing, and in which the adapter housing is sized to allow a portion of said adapter housing to be slid over the end of said battery housing to deploy said prongs for interconnection with said power supply.

14. An instrument system as recited in claim 13, wherein said at least one adapter includes interlock means for preventing said set of prongs from being deployed from said adapter housing after attachment of said adapter to said battery housing.

15. An instrument system as recited in claim 14, wherein said adapter housing includes a bottom surface, said interlock means including a pair of spaced openings in said bottom surface which are initially misaligned with said prongs when said adapter is in a first attachment position, said adapter being rotatable to allow said prongs to be aligned with said openings when said adapter has been rotated to a second attachment position.

16. An instrument system as recited in claim 14, wherein said interlock means includes at least one pin member interconnecting said adapter housing and said recharging means and preventing relative movement therebetween and actuable switch means disposed on the exterior of said adapter housing connected to said pin member for selectively disconnecting said adapter housing from said recharging means and allowing said prongs to be exposed.

17. An instrument system as recited in claim 11, wherein said releasable engagement means includes a T-shaped attachment member provided on said one end of at least one battery-charging adapter for releasably engaging a keyway provided on the second end of said battery housing.

18. An instrument system as recited in claim 11, wherein said releasable engagement means includes an attachment member provided on one of said battery housing and said adapter for engaging an opening provided on the other of said housing and said adapter.

19. A battery-charging adapter for a hand-held medical diagnostic instrument, said diagnostic instrument comprising a handle portion having a first end attached to an instrument head and an opposing second end, said handle portion including an interior containing at least one rechargeable battery for powering said instrument head and permitting examination of a medical target, said adapter comprising:

an adapter housing;

recharging means for recharging said at least one rechargeable battery disposed within said handle portion;

releasable attachment means for releasably attaching said adapter to said second end of said handle portion wherein said recharging means includes a transformer and a set of prongs extending from said transformer for engaging a power supply; and means for selectively deploying said prongs from one end of said adapter housing after said adapter has been attached to said handle portion and in which said adapter forms part of said handle portion of said medical diagnostic instrument.

20. An adapter as recited in claim 19, wherein said adapter housing includes a hollow interior into which said recharging means are disposed, said adapter housing being slidingly movable relative to said recharging means to permit deployment of said prongs from said adapter housing.

21. An adapter as recited in claim 20, wherein said releasable attachment means are interconnected to said recharging means such that said transformer and said set of extending prongs are fixed axially when said adapter is attached to said handle portion, the adapter housing being sized to allow at least a portion of said adapter housing to be slid over the end of said handle portion and exposing said set of prongs for interconnection with said power supply.

22. An adapter as recited in claim 21, including interlock means for preventing said set of prongs from being deployed from said adapter housing after attachment of said adapter to said handle portion.

23. An adapter as recited in claim 22, wherein said adapter housing includes a bottom surface, said interlock means including a pair of spaced openings in said bottom surface which are initially misaligned with said prongs when said adapter is in a first attachment position, said adapter being rotatable to allow said prongs to be aligned with said openings when said adapter has been rotated to a second attachment position.

24. An adapter as recited in claim 22, wherein said interlock means includes at least one pin member interconnecting said adapter housing and said recharging means and preventing relative movement therebetween and actuable switch means disposed on the exterior of said adapter housing connected to said pin member for selectively disconnecting said adapter housing from said recharging means and allowing said prongs to be exposed.

25. An adapter as recited in claim 19, wherein said releasable attachment means includes a T-shaped engagement member provided on said one end of said adapter housing for releasably engaging a keyway provided on the handle portion.

26. An adapter as recited in claim 19, wherein said releasable attachment means includes an attachment member provided on one of said handle portion and said adapter for engaging an opening provided on the other of said and said adapter.

27. A method of recharging batteries contained in a hand-held diagnostic instrument handle, said method comprising the steps of:

attaching a battery-charging adapter to one end of said instrument handle, said adapter including an adapter housing, means for releasably attaching said adapter housing to said handle end, and recharging means for recharging at least one battery contained in said handle, said recharging means including a transformer and a set of prongs extending from said transformer;

selectively deploying the set of prongs from said adapter housing;

attaching said prongs to an exterior power supply;

recharging said battery;

detaching said prongs from the exterior power supply; and retracting said prongs into the interior of said adapter housing, thereby permitting the adapter to be used as part of the handle of the instrument.

28. A method according to claim 27, wherein said releasable attaching means are interconnected to said recharging means so as to fix said recharging means relative to said handle, said method further including the step of:

sliding a portion of said charging adapter over said handle to expose said prongs after said attaching step.

29. A method according to claim 28, wherein said recharging means and said adapter housing are releasably interlocked, said method including the step of:

releasing the interlock said adapter housing from said recharging means to allow relative movement therebetween prior to said sliding step.

30. A method according to claim 29, wherein said releasing step includes the step of:

rotating said adapter about a common center axis of said adapter and said handle to align said prongs with a set of slitted openings in the bottom of said adapter housing.

31. A method according to claim 29, wherein said releasing step includes the step of:

depressing an actuable button on said adapter housing to release said adapter housing from said recharging means.

* * * * *